(12) United States Patent
Esmaeili

(10) Patent No.: US 7,643,136 B2
(45) Date of Patent: Jan. 5, 2010

(54) DEVICE FOR INSPECTION OF NARROW SPACES AND OBJECTS IN NARROW SPACES

(75) Inventor: Sasan Esmaeili, Solna (SE)

(73) Assignee: Optilia Instrument AB, Sollentuna (SE)

( * ) Notice: Subject to any disclaimer, the term of this patent is extended or adjusted under 35 U.S.C. 154(b) by 264 days.

(21) Appl. No.: 11/346,525

(22) Filed: Feb. 2, 2006

(65) Prior Publication Data

US 2007/0177138 A1 Aug. 2, 2007

(51) Int. Cl.
*G01N 21/00* (2006.01)

(52) U.S. Cl. ............... 356/237.1; 356/237.5; 356/241.1

(58) Field of Classification Search ... 356/237.1–237.5, 356/241.1–241.4; 348/65, 124; 359/798
See application file for complete search history.

(56) References Cited

U.S. PATENT DOCUMENTS

| 4,686,565 A | * | 8/1987 | Ando ........................ 348/126 |
| 4,795,237 A | * | 1/1989 | Kempf ....................... 359/726 |
| 5,052,802 A | * | 10/1991 | Hayes et al. .............. 356/237.1 |
| 5,613,936 A | * | 3/1997 | Czarnek et al. ............. 600/166 |
| 5,644,438 A | * | 7/1997 | Pottash ....................... 359/798 |
| 5,856,874 A | * | 1/1999 | Tachibana et al. ........... 356/613 |
| 6,043,876 A | * | 3/2000 | Holliday et al. .......... 356/237.1 |
| 6,580,501 B2 | | 6/2003 | Cannon |

* cited by examiner

*Primary Examiner*—Hoa Q Pham
(74) *Attorney, Agent, or Firm*—Potomac Patent Group PLLC

(57) ABSTRACT

A device for visual inspection of narrow spaces and objects located in narrow spaces such as solder joints between a component and a printed circuit board has an image prism for deflecting light from the spaces and objects to be inspected and an image sensor that can be connected to a display. For illuminating the solder joints light sources are provided that are located at the transmission path of light from the image prism to the image sensor. The light sources are connected to light guides having outlet ends that are located to issue light at the sides of the light entrance surface of the image prism. Special illumination prisms can be provided to direct the light. The issued light is directed to the field of view, if desired in directions obliquely down into the surface at which the spaces or objects are located and in a weakly converging fashion. Extra light sources can be connected to light guides of a background illumination unit. The light guides may be part of an illuminating unit that can be attached the rest of the device by a snapping function.

43 Claims, 8 Drawing Sheets

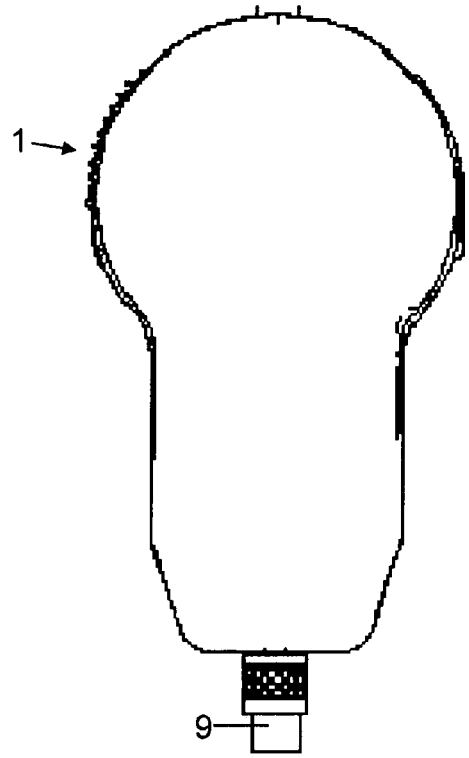
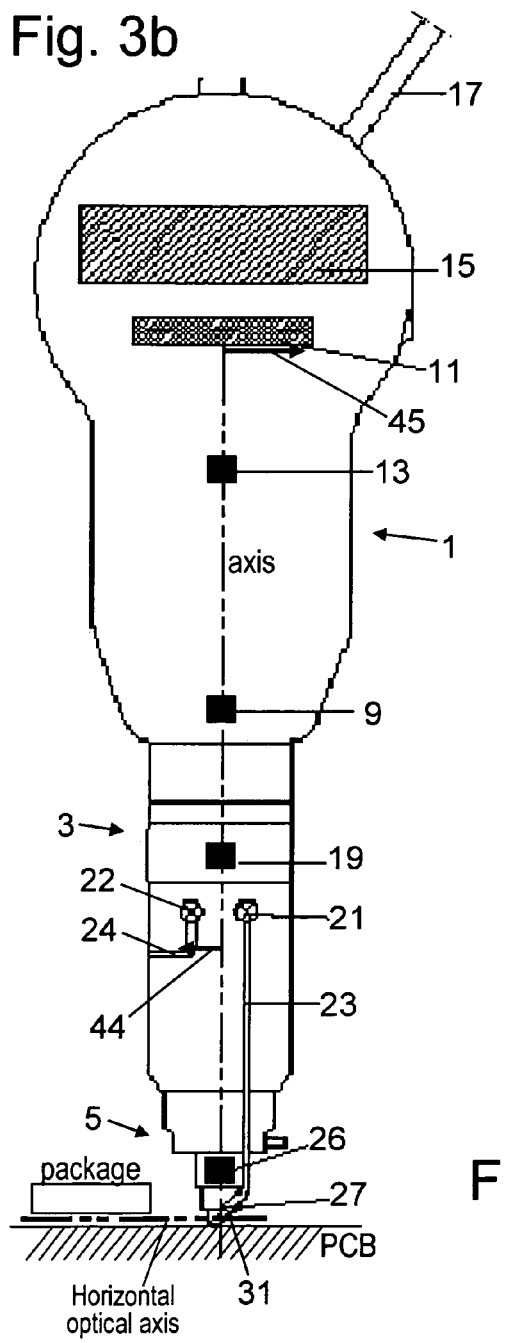
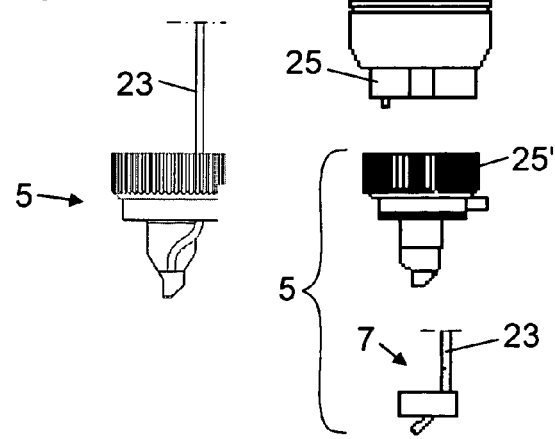

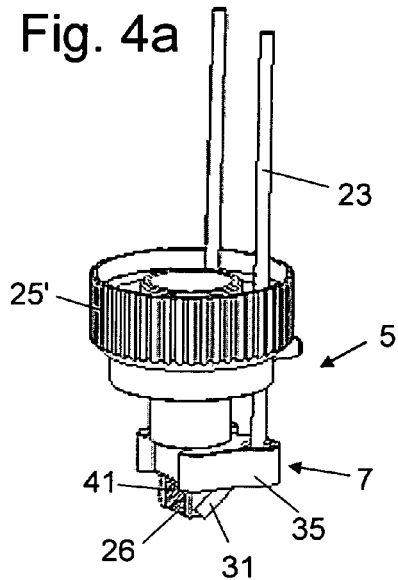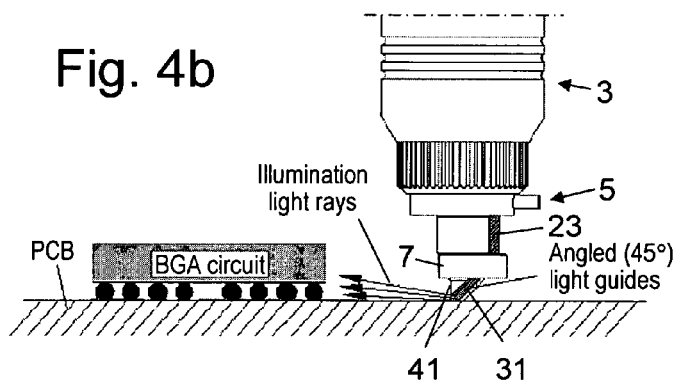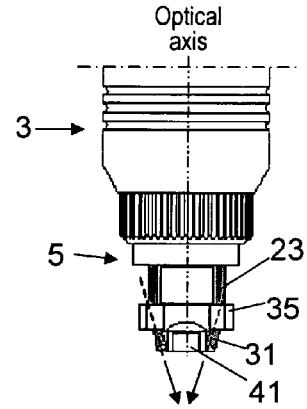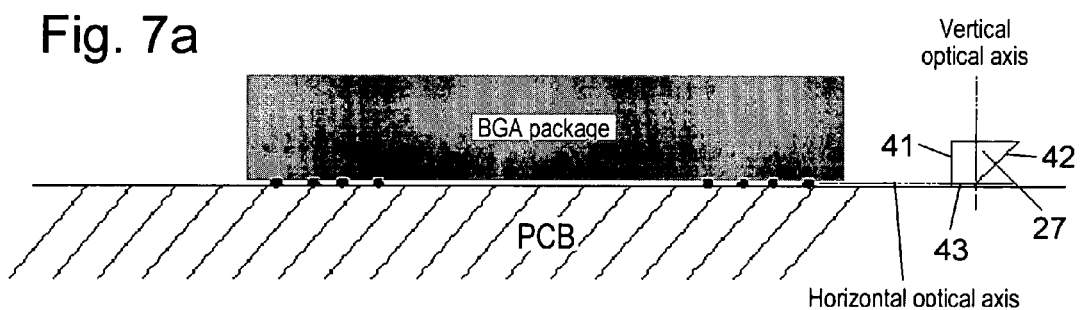

Fig. 6a
Fig. 6b
Fig. 6c
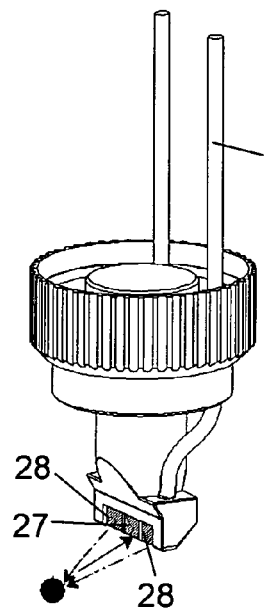
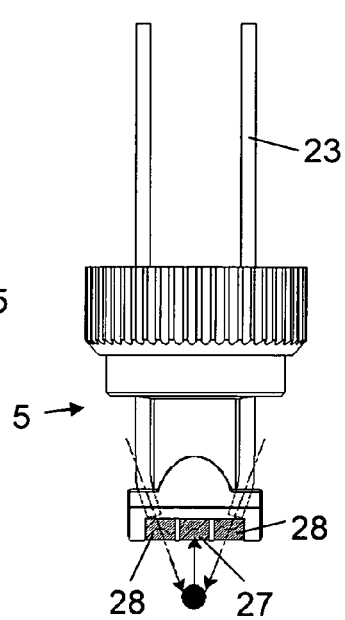
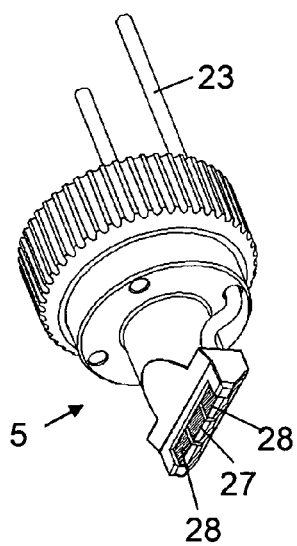
Fig. 6d
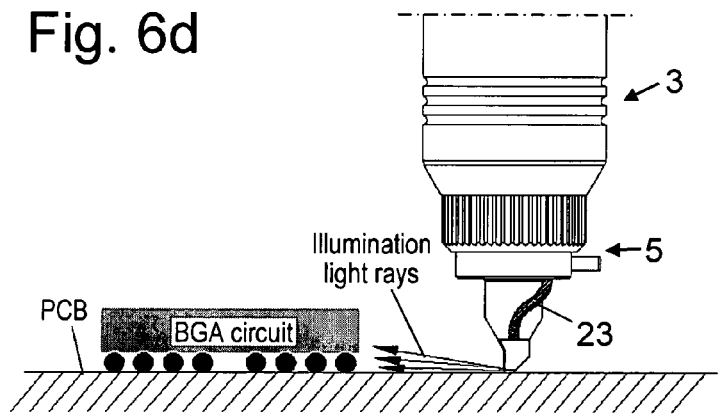
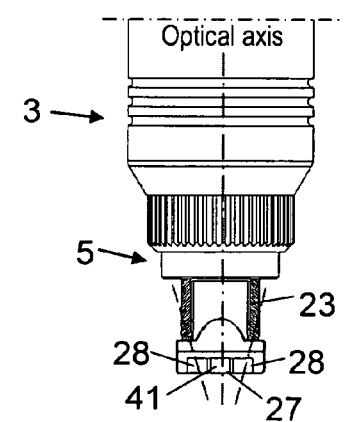
Fig. 6e

DEVICE FOR INSPECTION OF NARROW SPACES AND OBJECTS IN NARROW SPACES

TECHNICAL FIELD

The present invention relates generally to video microscopes and particularly to a device for visual inspection of narrow spaces located at surfaces and object located in such narrow spaces, such as for visual inspection of spaces between an electric or electronic component and a printed circuit board and in particular solder joints located in such spaces or generally spaces between two electronic components and objects located therein. It relates in particular to a video microscope having illumination for capturing images of solder joints under electronic packages or chips such as BGA packages or of other objects located in small, low or narrow spaces, and for generating a corresponding signal for e.g. displaying the captured images on some display unit such as a TV monitor or a computer monitor.

BACKGROUND

When using BGA (Ball Grid Array) packages as components on electronic circuit boards an inspection of solder joints of these components is necessary in many cases. Solder bonds of BGA packages are hidden under the package or circuit, and hence a reliable inspection of solder joints has been a difficult task for many companies assembling circuit boards. Hence, during the two past decades, several X-rays systems have been developed for inspection of BGA packages. Using the results of such inspections, assembler companies have been able to better control the quality and condition of the solder joints.

However, the complexity, the limitations, such as the lack of capability of detecting "cold" solder joints, cracks, thermal stress, flux agent residues, etc., and the high cost of X-ray systems, typically in the range of EUR40 000 to EUR100 000, have made visual inspection systems be an attractive alternative or complement to X-ray systems. The need for visual inspection of BGA and similar packages is constantly increasing within the electronic circuit manufacturing industry since more and more BGA, MicroBGA, CSP and Flip-Chip packages are designed and assembled on PCBs (Printed Circuit Boards). The visual inspection systems are becoming efficient, cost effective and reliable besides the X-ray systems, even bringing advantages that the X-ray systems do not offer.

Optical systems for inspection of BGA joints like Ersascope manufactured and sold by Ersa GmbH or VPI-optical Inspection System manufactured by Metcal in Menlo Park, Calif., have been on the market for a few years. However, the video microscopes according to the prior art can, due to their designs, only be used stationarily in laboratories and they have not such a degree of integration that they can be used as mobile equipment, without extra requirements such as of being connected to a stand and/or to external illumination sources and/or other necessary accessories or devices.

U.S. Pat. No. 6,580,501 for Cannon and assigned to Ersa GmbH discloses stationary apparatus for visual inspection of concealed solder joints, the apparatus including a lens head, an ocular unit and an image transmission unit for transmitting the image from the lens head to the ocular unit and having the basic structure and shape of an industrial or medical endoscope. The lens head comprises a housing having a recess in which a light deflecting prism is mounted. An illumination device has light exits located at opposite sides of the prism, the light exits being the free ends of the fibers of a glass fiber bundle, the fibers connected to a single external light source at their other ends. The light exits issue light in directions parallel to the surface of the PCB which is to be inspected.

SUMMARY

It is an object of the invention to provide a device for inspecting narrow spaces and/or objects located in narrow spaces at a surface that has an efficient design of its illumination components.

Problems to which the invention may provide solutions include how to design a device for inspecting narrow spaces and/or objects located in narrow spaces such as solder joints of electronic packages to make the inspecting efficient, how to design the device so that it can be easily handled and moved to any location where it is to be used, how to design the device so that the optical head of the device, which may be the fragile part of such devices and hence can be broken or damaged during operation, can be exchanged easily and quickly, and in particular how to provide illuminating light to the spaces and/or objects such as joints that are to be inspected.

Generally, such a device for visual inspection of narrow spaces and/or objects located in narrow spaces such as solder joints between an electric or electronic component and a printed circuit board may in particular include an optical head that includes one image prism for deflecting light and having an entrance opening for light. The device may further include an objective lens system for creating a picture or image from light deflected by the image prism, and a basic camera unit that in turn may include an optical system such as a lens system and an image sensor detecting light rays deflected by the image prism, as collected by the objective lens system and imaged by the optical system of the basic camera unit. Furthermore, the device may include an illuminating part or illuminating parts for illuminating the narrow spaces and/or objects to be inspected. The image sensor can be connected to a display. A plurality of light sources may be located internally, close to or at the transmission path of light from the image prism to the image sensor. The light sources may be connected to upper ends of light guides such as light guiding fibers in the optical head, the light guides having lower ends located at the light entrance surface of the image prism or at the light entrance surfaces of special illumination prisms to issue light directed towards the spaces and/or objects to be inspected, in particular e.g. light converging or weakly converging to the field of view. The issued light may if desired also be directed obliquely down into the surface of a substrate such as a circuit board, the solder joints of which are to be inspected. The issued light may be issued in a converging way, such as a slightly or weakly converging way, towards the objects to be inspected or into the space to be inspected.

The device may have a modular de sign which in some cases can make inspection of e.g. BGAs easier, quicker and more cost effective. Thus, the device can be composed of a first module, called an optical head module or unit containing an objective lens system, light ray deflecting prisms and illumination light guides, a second module, called a lens module, and a third module, called a basic camera module. The modules and the part or parts for providing the illuminating are mounted to each other when using the device and they can be detached from each other for e.g. exchanging them for similar modules such as modules holding optical lens systems of other magnifications or optical heads having other geometrical configurations.

Furthermore, the device may have or include one or more of the following features:

a. Integration of light sources, e.g. LEDs, with the lens module. This feature eliminates the need for external light sources and allows a compact and mobile design of the inspecting device. It also allows that the device does not necessarily have to be connected to a stand, a stationary illumination light source or other external devices for operation, except some display, Thus, the device can in a basic design be simply operated by one hand of a person and can thereby be moved to any location for inspection.

b. The illumination part or parts of the optical head module may have exits for light which are located in an angle of 30°-60°, preferably about 45°, to the surface at which the spaces and/or objects to be inspected are located. The exits may in addition or alternatively have a 10-20° tilt of the axes of the issued light in two different planes. This may provide an at least weakly converging, sufficient illumination of the central area of a field to be inspected.

c. The illumination parts of the optical head module may be configured as a detachable illumination unit having a snapping function allowing an easy and quick connection/disconnection of the illumination unit to the rest of the device.

d. The illumination parts of the optical head module may include two light guides for guiding illumination light from two internal light sources to two illumination prisms, e.g. right angle prisms, similar to the image prism and e.g. mounted in the same horizontal position as but separately from the image prism, for deflecting illumination light rays into the spaces to be inspected, such the narrow space between a BGA component and a PCB surface.

e. The image prism that may be a right angle prism has an optical axis for incoming light located at a very low position close to the surface at which the spaces and/or objects to be inspected are located. It allows an efficient collection of image forming rays, diverging from e.g. the very small gap between the surface of a PCB and the bottom surface of a package or component mounted thereto.

f. Each of the illumination prisms that may also be right angle prisms may have an optical axis for exiting illumination light which axis is located at a very low position close to the surface at which the narrow spaces and/or objects to be inspected are located. It allows an efficient illumination into e.g. the very small gap between the surface of a PCB and the bottom surface of a package or component mounted thereto.

g. The modular design of the device may e.g. allow an easy and quick exchange of parts needed for illumination such as light guides, such as in the case of damage or aging.

h. The modular design of the device may also allow an easy and quick exchange of optical head modules if e.g. other magnifications or other geometrical configurations are desired.

i. The modular design of the device may further allow an easy and quick exchange of the entire side viewing lens module, including the optical head module and the special narrow space illumination, to e.g. lens units having a standard zoom or including fixed focal length lenses for other regular inspection applications in addition to e.g. inspecting narrow spaces and/or objects located in narrow spaces such as solder balls of BGAs.

j. Two extra LED light source outputs may if desired be provided on the lens module and/or on optical head modules. It can make it possible to attach extra light guides to the device for background illumination of e.g. BGA solder balls from another side of an electronic package or for extra scene illumination of other objects which are to be inspected.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

While the novel features of the invention are set forth with particularly in the appended claims, a complete understanding of the invention, both as to organization and content, and of the above and other features thereof may be gained from and the invention will be better appreciated from a consideration of the following detailed description of non-limiting embodiments presented hereinbelow with reference to the accompanying drawings, in which:

FIG. 3*a* is an exploded, schematic view of a device for visual inspection,

FIG. 3*b* is a schematic view of the assembled device of FIG. 3*a*,

FIG. 3*c* is a schematic view of an alternative optical head module for use in the device of FIGS. 3*a* and 3*b*, FIG. 4*a* is a perspective view of the optical head module of the device of FIGS. 3*a* and 3*b*, FIG. 4*b* is a picture illustrating illumination of solder balls using the device of FIGS. 3*a* and 3*b*, FIG. 4*c* is picture illustrating exit angles of illumination light for the device of FIGS. 3*a* and 3*b*, FIGS. 5*a*-5*d* are views illustrating an exchangeable illumination unit of the device of FIGS. 3*a* and 3*b*, FIGS. 6*a*-6*c* are views illustrating the alternative optical head module of FIG. 3*c*, FIG. 6*d* is a picture similar to FIG. 4*b* illustrating illumination of solder balls using the alternative optical head module, FIG. 6*e* is a picture similar to FIG. 4*c* illustrating exit angles of illumination light using the alternative optical head module, FIG. 7*a* is a side view of image and illumination prisms, FIG. 7*b* is a perspective view of the prisms of FIG. 7*a*, FIG. 8*a* a schematic view illustrating how to use the device of FIGS. 3*a*-6*e*.

DETAILED DESCRIPTION

Figure 1A:
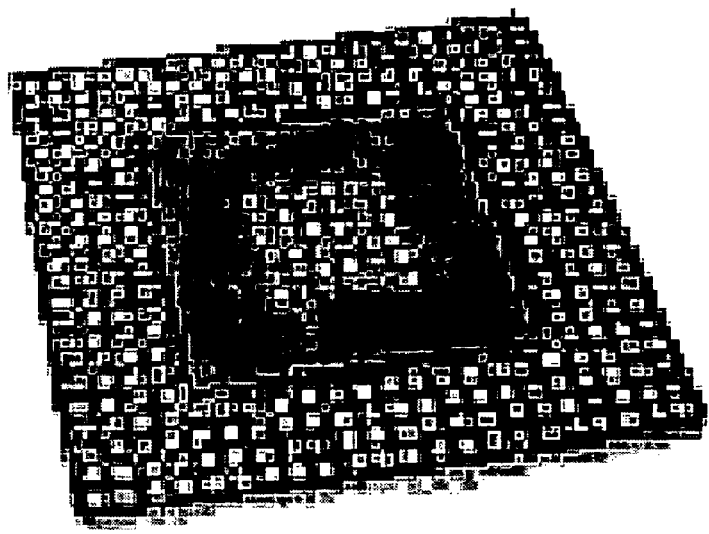
FIG. 1*a* is a perspective view of a BGA Circuit.
Figure 1B:
FIG. 1*b* is a photograph of solder balls under a BGA package.
Figure 2A:
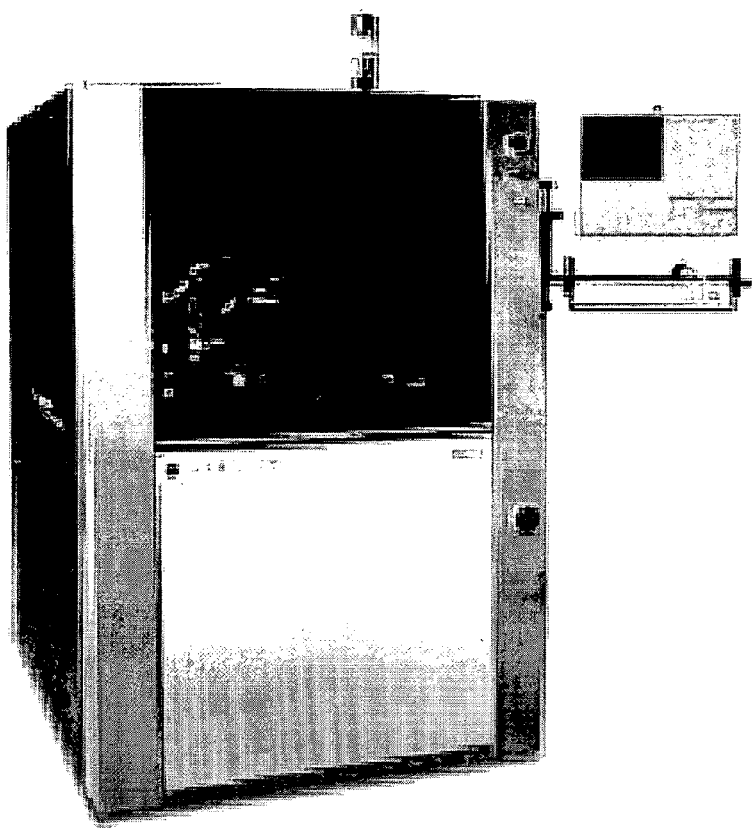
FIG. 2*a* is a perspective view of X-ray equipment for BGA inspection.
Figure 2B:
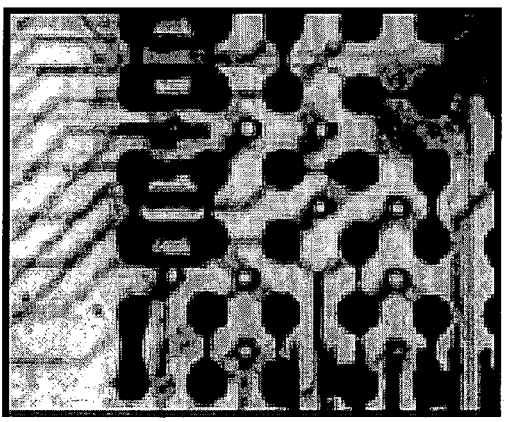
FIGS. 2*b*-2*c* are X-ray pictures of solder balls.
Figure 2C:
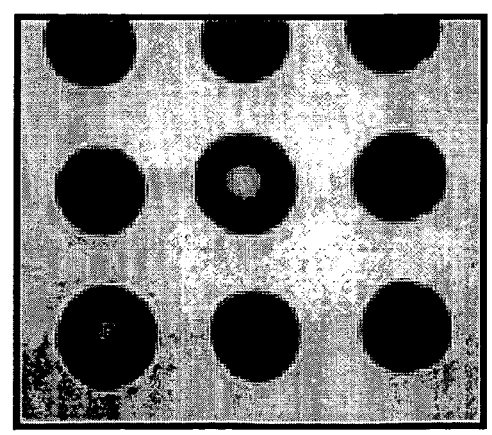
Figure 5A:
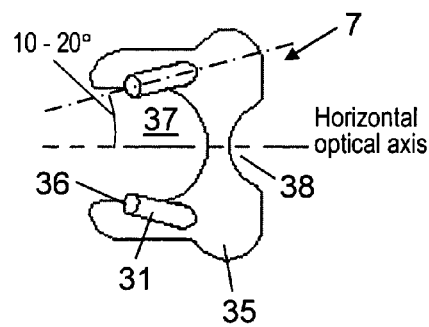
Figure 5B:
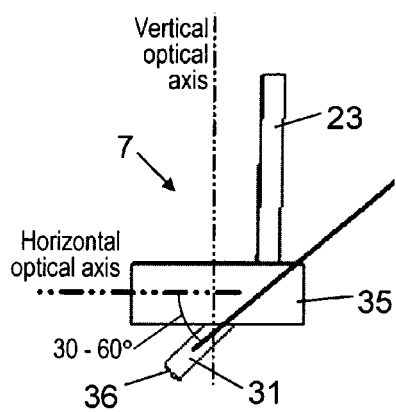
Figure 5C:
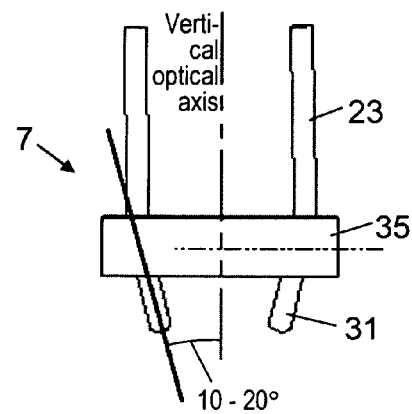
Figure 5D:
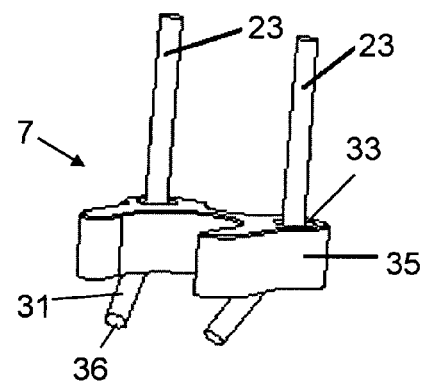
Figure 8A:
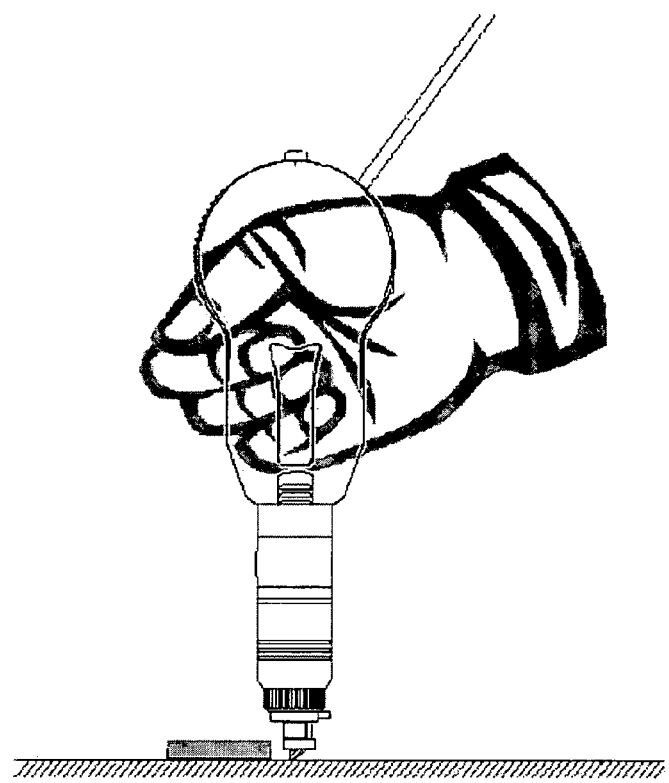
FIG. 8*b* is a real photograph illustrating how to use the device of FIGS. 3*a*-6*e*.
Figure 8B:
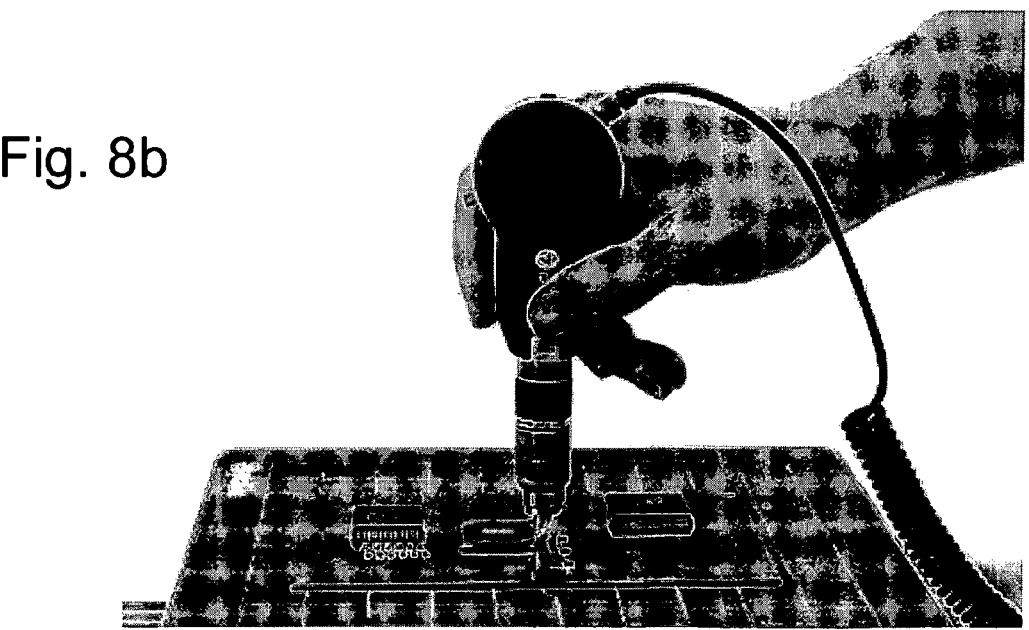

In FIGS. 8*a* and 8*b* a device is illustrated that is suitable for inspecting narrow spaces such as paces between a component and the surface of a substrate to which the component is mounted, such as for inspecting solder joints of electronic components or chips, e.g. BGA-MicroBGA, CSP and Flip-Chip packages, and other electric and electronic components, on circuit boards, e.g. printed circuit boards (PCBs). As appears from the figures the device may designed to be mobile and to be easily handled in any location, e.g. by a single hand of an operator, but it may also be used in a stationary place if attached to a suitable stand, not shown. Also, the device may have an efficient, built-in illumination for illuminating the spaces and objects, e.g. solder joints, to be inspected. In particular, the device may comprise a basic camera unit, a detachable lens unit and a detachable optical head.

The device as illustrated also in FIGS. 3a-6d is designed primarily for inspection of solder joints of surface mounted (SMT) and similar components such as BGA packages. It includes basically three exchangeable modules, a camera module 1, a lens module 3 and an optical head module or optical head unit 5.

The camera module 1 includes an upper exchangeable objective lens 9, an image sensor 11, a lens 13 for transporting images further back from the upper objective lens to the active area of the image sensor, an electronic control unit 15, a cable indicated at 17 to supply power to the inspection device and to connect it to a display, not shown, for displaying captured images. The camera module is designed to create images of any object at a specific magnification. The lens module 3 includes a focusing lens 19, a plurality of light sources 21, 22 such as LEDs, some thereof not shown, and electronic circuits, not shown, needed for driving them.

The optical head module or unit 5 includes illumination light guides 23 connected at upper or inlet ends to first ones of the light sources 21, also called illumination light sources, for conducting light generated by these light sources to suitable outlets at the optical head module or unit. In a first embodiment of the optical head module or unit seen in FIGS. 3a, 3b, 4a, 4b, 4c and 9 the illumination light guides 23 are specifically included in a light guide unit 7 in turn included in or attached to the optical head module or unit. Other light guides 24 may be provided for conducting light from second ones 22 of the light sources to other illumination devices, not shown in these figures. The illumination light guides 23 may pass in bores, not shown, inside the lens module 3 and the optical head module or unit 5 and have adapted lengths to be capable of receiving light issued from the respective light sources 21.

Since separate light sources are provided, one for each of the light guides, the intensity of the light sources can be controlled separately from and independently of each other and thereby also the light issued from the different illumination issuing points of the optical head module or unit can be controlled. By locating the light sources in the illustrated way, at the transmission path of image forming light from the optical head module or unit 5 to the image sensor 11, a compact device is obtained having not requiring connection to an external light source.

E.g. a total of four light sources can be provided, two thereof connected to the illumination light guides 23 and two to the other light guides 24. The lens module 3 has at its lower ends a thread 25 for attaching it to or for attaching to it one of the optical head modules or units 5, using a collar nut 25' at the upper part of the optical head modules or units and cooperating with the thread of the lens module. Each of the optical head modules or units includes a series of lenses forming a lower objective lens or lower lens assembly 26 and it further includes a specially designed image prism 27 for reflecting incoming light by 90°. Finally, it includes in the first embodiment the exchangeable light guide unit 7, also called illuminating unit, for guiding illumination light from the illumination light guides 23 in a direction towards the object or space to be inspected. The illumination light is issued from places at each side of the image prism, in the first embodiment directly from the lower or outlet ends 36 of the illumination light guides.

The light guide unit 7, see FIGS. 5a-5d, includes the two illumination light guides 23, having outlet portions or end portions 31 that are substantially straight and extend in angles of approximately 45°, generally in the range of 30°-60°, in relation to the longitudinal or basic optical axis of the device, i.e. to a vertical direction as seen in FIGS. 3a-9, and/or in relation to the surface at which the joints to be inspected are located. The illumination light guides extend through bores 33 in a brace or holder 35 and are firmly attached thereto. The holder has a snapping function for attaching/detaching it to a portion of the optical head module or unit 5, this function provided by the shape of the holder. Thus, the holder 35 is configured, see in particular FIG. 8a, to have a body including a part-circular recess 37, as observed in the axis or longitudinal direction of the device. The recess walls or profile correspond/s/ to somewhat more than 180° such as about 200° to be capable of cooperating with and enclosing a cylindrical outer surface of the optical head module or unit 5 in order to be attached to this module or unit. Opposite the recess 37 the body has another smaller, shallower recess 38 resulting in a weakened portion of the body that assists in the snapping action.

The bores 33 are located so that the ends or light outlets 36 of the illumination light guides 23 will be placed at the two opposite sides of the entrance surface of the image prism 27 of the optical head module or unit 5, when the light guide unit is mounted thereto. Hence, the illumination light rays emitted from the illumination light sources 21 pass the illumination light guides to exit therefrom next to or at the sides of the clear aperture of the entrance surface 41 of the image prism 27, see FIGS. 7a and 7b, for illuminating the space or object/objects to be inspected, e.g. in a parallel or weakly converging way. The light rays issued from the ends of the illumination light guides may pass in approximately angles of 45°, generally in the range of 30°-60°, in relation to the plane of the surface of a substrate such as a PCB at which e.g. an object such as electronic package is mounted and in relation to the longitudinal, vertical axis of the device and in approximate angles of 10-20° as observed along the vertical optical axis of the lens system in relation to a horizontal optical axis of the device, this latter axis being in principle perpendicular to the entrance surface 41 of the image prism 27, and/or as observed from a point in front of the entrance surface 41 of the image prism 27 when the device is used for inspection and the light guide unit 7 is attached in the optical head module or unit 5, i.e. in approximate angles of 10-20° as observed along a horizontal optical axis of the optical system in relation to the vertical axis of the device. Consequently, the illuminating light rays are introduced into the desired space, i.e. the gap between the object to be inspected such as a BGA package and the PCB and are directed to the middle of the object field of the lower objective lens assembly 26 in a converging way.

In another embodiment of the optical head module or unit 5, see FIGS. 3c and 6a-6e, the optical head module or unit 5 is a single unit. At the image prism 27 two illumination prisms 28 are arranged that are located in the same plane as the image prism and placed separately and symmetrically at two opposite sides of the image prism for reflecting illumination light from the illumination light guides 23 in a suitable angle of e.g. 90° to pass in a direction towards the object or space to be inspected. The two illumination prisms 28 may be identical to each other and they may also be identical to the image prism 27. E.g. at least the illumination prisms may be mounted to have their upper surfaces located in a first plane, and they may also have their front surfaces located in a single second plane perpendicular to the first plane. The oblique surfaces of the prisms may also be all located in the same oblique plane, this plane located in a suitable angle such as about 45° to the first and second planes. The same may be true also for the image prism 27.

Generally, the illumination prisms 28 may preferably be optically unconnected to or optically separated from each other and/or optically isolated from the image prism 27. Also, the illumination prisms may be optically isolated from all parts of the entire image forming optical system of the device. Furthermore, each of the illumination prisms may receive light from a single dedicated illumination light source, the light being guided through e.g. one ore possibly more illumination light guides from the dedicated light source.

In this embodiment, the lower ends of the illumination light guides are located at the upper surfaces of the illumination prisms 28 which thus are the entrance surfaces of these prisms, see also FIG. 7b. The end portions of the illumination light guides 23 may be located or directed in some suitable angles to give angles of incidence of about 10° in relation to the normal of the entrance surface taken in a plane parallel to the exit surfaces of the illumination prisms 28, i.e. as seen from a point in front of the entrance surface 41 of the image prism 27 or the exit surfaces of the illumination prisms 28. Hence, the exiting light rays may be somewhat converging. Such a converging effect can also be achieved by arranging the end portions of the illumination light guides 23 perpendicularly to the entrance of surfaces of the illuminating prisms and appropriately locating and/or configuring the illumination prisms 28 as is obvious to any person skilled in the art.

The right angle image prism 27 and also the illumination prisms 28 are specially designed and arranged to obtain, see FIGS. 7a-7b, an optical axis, also called horizontal optical axis, prior to the reflecting surface, i.e. the hypotenuse surface 42, for light rays parallel to the surface of the substrate or PCB at a distance of approximately 0.1-0.2 mm from the bottom surface 43 of the prism, i.e. also from the substrate or PCB surface. This design places the optical axis for incoming light and issued illuminating light at a very low position, below the bottom surfaces of e.g. mounted BGA packages, and makes it possible to collect image-building light rays coming from solder balls by the lower objective lens system 26 inside the respective optical head module or unit 5.

The bottom surface 43, that can also be called a lower flat surface, thus connects the entrance surface 41 and the reflecting or deflecting surface 42 of the image prism 27 and for the illumination prisms 28, it connects the exit surface and reflecting surface. This bottom surface is basically the only portion of the device contacting, when the device is used for visual inspection of narrow spaces and/or objects in narrow spaces, the surface at which the narrow spaces or objects are located. The bottom surface 43 may further be designed to have a width sufficient to avoid a mechanical contact along only a single line with said surface at which the narrow spaces or objects are located, this design preventing unnecessary friction and damages to this surface and also to the bottom surface 43. The width is defined as the distance between the edge of the bottom surface at the entrance surface 41 and the edge at the reflecting surface 42 of the image prism 27. For illumination prisms 28, it is defined as the distance between the edge of the bottom surface at the exit surface and the edge at the reflecting surface. The lower flat surface may e.g. have a width in the range of 0.2-0.6 mm. Prisms having different widths give also different heights of the horizontal optical axis if other components of the optical system of the inspection are unchanged. In a typical embodiment e.g. a lower flat surface having a width of 0.5 mm can give a height of about 0.2 mm from the substrate or PCB surface whereas a width of 0.6 mm can give a height of about 0.1 mm when the device is used. Optical head modules 5 having prisms of such different designs may thus be provided, adapted to the height of spaces or objects to be inspected.

A real image of an object such as solder balls, which is also the primary image 44, see FIG. 3a, is created in the image space of the lower objective lens 26 at the same position as the object plane of the upper objective lens 9 in the camera module 1 together with the focusing lens 19 of the lens module 3. A secondary real image 45 of the solder balls is then created on the image sensor 11 of the camera module 1. Optical magnification as well as the object distance of the optical system of the device can be changed by moving the focusing lens package 19 along the optical axis in the lens module 3. The size of the images of the solder balls as well as the object distance, i.e. the focusing distance, of the device can be changed due to this configuration. This is essential for inspecting solder balls at second, third and deeper positions, underneath the electronic package to be inspected.

Figure 9:
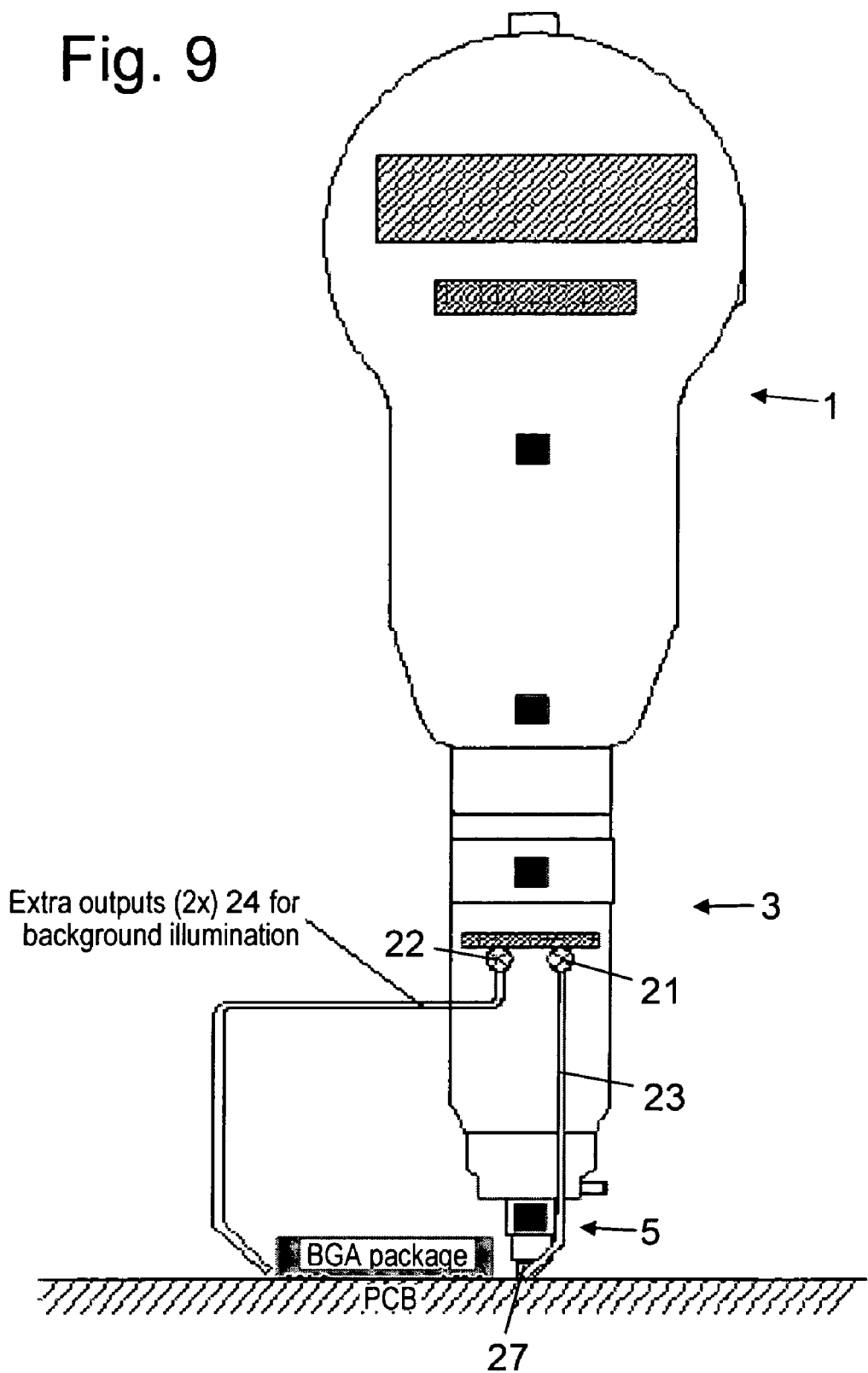
FIG. 9 is schematic view illustrating extra illumination outputs from internal light sources of the device of FIGS. 3*a*-6*e*.

The background illumination is illustrated in FIG. 9. It is seen that the extra light sources 22 emit light into the extra light guides 24 to exit at a side of a BGA package that e.g. is opposite the side at which the image prism 27 and the exits of the ordinary illumination light guides 23 of the device are located.

It is obvious to one skilled in the art that in some embodiments of the inspection device as described herein, instead of using prisms for deflecting light other light deflecting or light reflecting devices can be used such as devices having one or more reflecting surfaces, in particular mirrors, e.g. provided as components or as reflecting surfaces of other parts of the optical head. E.g. the image prism can generally be replaced with an image ray deflecting device, this being an image ray reflecting device if it is the reflection type, and the illumination prisms with illumination light deflecting devices, being illumination light reflecting devices if they are the reflecting type. Such deflecting devices then have entrance openings or entrance sides, at which light comes in or hits the devices to be then deflected, and exit openings or exit sides at which light deflected by the devices leaves or goes out from the devices. The entrance openings or sides correspond to the entrance surfaces of light deflecting prisms, as defined above, and the exit openings or sides correspond to the exit surfaces of prisms used for light deflection.

It should be understood herein and in the claims hereof that such terms as "top", "bottom", "lower", "upper", "horizontal", "vertical", "height" and the like have been used for illustration purposes only, in order to provide a clear and understandable description and claiming of the invention. Such terms are not in any way to be construed as limiting, because the devices of invention are omni-directional in use as can be understood by their various uses in different application fields.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention.

Numerous other embodiments may be envisaged without departing from the spirit and scope of the invention.

What is claimed is:

1. A device for visual inspection of narrow spaces and objects in narrow spaces at substrate surfaces including:
    an image ray deflecting device for deflecting light having an entrance opening or side for light,
    an image sensor for detecting light deflected by the image ray deflecting device, and
    an illumination system for illuminating the narrow spaces or the object or objects to be inspected, the illuminating system including
    light sources located internally in the device, and close to or at the transmission path of light from the image ray deflecting device to the image sensor, and
    light guides, the light sources directly connected to upper ends of the light guides, the light guides extending substantially from the light sources down to the vicinity of the image ray deflecting device, and lower ends of the light guides arranged or connected to issue illuminating light at the sides of or from points located at the sides of the light entrance opening or side of the image ray deflecting device, wherein the light guides have lower end portions directing light from their lower end surfaces in directions having a tilt in the range of 10-20° in relation to a longitudinal axis of the device seen in the direction of an axis of light incoming to and deflected by the image ray deflecting device.

2. The device of claim 1, wherein the lower or outlet ends of the light guides are located at the sides of the light entrance opening or side of the image ray deflecting device.

3. The device of claim 1, wherein the light guides have lower end portions directing light from their lower end surfaces in directions in the range of 30°-60° in relation to the surface of a substrate when the device is used for visual inspection of a narrow space or an object or objects in a narrow space at the substrate surface.

4. The device of claim 1, wherein the light guides have lower end portions directing light from their lower end surfaces in directions having a tilt in the range of 10-20° in relation to an axis of light incoming to and deflected by the image ray deflecting device seen in the direction along a longitudinal axis of the device.

5. The device of claim 1, further comprising an illuminating unit holding the light guides, the illuminating unit being detachable from the rest of the device.

6. The device of claim 5, wherein the illuminating unit has a body configured to be capable of attaching the body by a releasable snapping function to an adapted part of the device, the light guides mounted to the body.

7. The device of claim 6, wherein the body has a recess partly enclosing said adapted part of the device.

8. The device of claim 7, wherein the body is configured to have a weakened portion at a center of the recess to allow an elastic movement of parts of the body in relation to each other and thereby allowing the walls of the recess located at opposite sides of the recess to move in relation to each other to achieve the snapping function.

9. The device of claim 1, wherein the illumination system includes illumination light deflecting devices for deflecting illumination light received at entrance surfaces from lower, outlet ends of the light guides to issue the illumination light from exit openings of the illumination light deflecting devices towards the spaces or the object or objects to be inspected.

10. The device of claim 1, wherein the image sensor is connectable to a display.

11. The device of claim 1, wherein the light sources are located at equal distances of the image ray deflecting device, distributed along a circumference of an intermediate part of the device.

12. The device of claim 1, wherein the intensity of the light sources can be controlled separately from and independently of each other.

13. The device of claim 1, further comprising extra light sources connected or connectable to light guides of a background or scene illumination unit.

14. The device of claim 1, wherein the extra light sources are located at the transmission path of light from the image ray deflecting device to the image sensor.

15. The device of claim 1, wherein the image ray deflecting device has a reflection surface located in an angle in the range of 30°-60° to an optical axis of light incoming to the image ray deflecting device or to an optical axis of light outgoing from the image ray deflecting device.

16. The device of claim 1, wherein the image ray deflecting device includes an image prism having a bottom surface being in contact with the surface of a substrate at which a space or an object or objects to be inspected are located, so that an optical axis of the image prism for incoming light is located at a distance of 0.1-0.2 mm from said bottom surface.

17. The device of claim 1, further comprising an optical system for creating an image from light deflected by the image ray deflecting device and for transporting the image to the image sensor.

18. The device of claim 17, wherein the optical system includes
    a lower objective lens assembly receiving light directly from the image ray deflecting device,
    a focusing lens for changing magnification and focusing distance of the lower objective lens assembly, and
    an upper objective lens assembly receiving light from the focusing lens, the image sensor receiving light from the upper objective lens assembly.

19. The device of claim 1, wherein the image ray deflecting device is part of a first exchangeable module detachably mounted to the rest of the device.

20. The device of claim 19, wherein the first module includes a lower objective lens assembly receiving light directly from the image ray deflecting device.

21. The device of claim 19, wherein the light sources are part of a second module to which the first module is detachably mounted.

22. The device of claim 21, wherein the second module includes a focusing system for changing the position and the size of the image created by the first module and for focusing it on the image sensor.

23. The device of claim 21, wherein the image sensor is part of third module to which the second module is detachably mounted.

24. The device of claim 23, wherein the third module includes an upper objective lens assembly.

25. A device for visual inspection of narrow spaces and objects in narrow spaces including:
    an image ray reflecting device for deflecting light, the image ray deflecting device having an entrance opening or side and an exit opening or side for light rays,
    an image sensor for detecting light deflected by the image ray reflecting device, and
    an illumination system for providing illumination light from light sources to the spaces or the object or objects to be inspected, the illumination system including
    light sources for issuing illumination light, light guides connected at upper ends to the light sources for guiding light issued from the light sources, and illumination light reflecting devices for reflecting illumination light received at entrance openings or sides from lower, outlet ends of the light guides to issue illumination light from exit openings or sides of the illumination light reflecting devices towards the spaces or the object or objects to be inspected, wherein the light guides have lower end portions at their lower ends directing light from lower end surfaces of the light guides into the entrance openings or sides of the illuminating light reflecting devices in an incident angle range of 0°-45° in relation to an optical axis of the device in a plane containing the optical axis of the device and parallel to the exit opening or side of the image ray reflecting device.

26. The device of claim 25, wherein the exit openings or sides of the illumination light reflecting devices are located at the entrance opening or side of the image ray reflecting device.

27. The device of claim 25, wherein the illumination light reflecting devices are located at two opposite end sides of the image ray reflecting device.

28. The device of claim 25, wherein the illumination light reflecting devices are optically unconnected to each other or optically separated from each other.

29. The device of claim 25, wherein the illumination light reflecting devices are optically isolated from the image ray reflecting device.

30. The device of claim 25, wherein the illumination light reflecting devices are optically isolated from an image forming optical system including the image ray reflecting device.

31. The device of claim 25, wherein each of the illumination light reflecting devices is connected to its dedicated illumination light source via its corresponding dedicated illumination light guide.

32. The device of claim 25, wherein bottom surfaces of the illumination light reflecting devices are located in the same plane or level as a bottom surface of the image ray reflecting device.

33. The device of claim 25, wherein each of the image ray reflecting device and the illumination light reflecting devices have a reflection surface located in an angle in the range of 30°-60° to the entrance opening or side and to the exit opening or side of the respective reflecting device.

34. The device of claim 25, wherein the image ray reflecting device and the illumination light reflecting devices include bottom surfaces being the only parts of the device coming in contact with a surface at which the space or object or objects to be inspected are located, so that the optical axis of the image ray reflecting device for incoming light is located at a distance of 0.1-0.2 mm from the bottom surface of the image ray reflecting device and the optical axes of the illumination light reflecting devices for outgoing light is located at a distance of 0.1-0.2 mm from the bottom surface of the respective illumination light reflecting device.

35. The device of claim 25, wherein the image ray reflecting device and the illumination light reflecting devices are parts of a first exchangeable module detachably mounted to the rest of the device.

36. A device for visual inspection of narrow spaces and objects in narrow spaces at substrate surfaces including:

an image ray reflecting device for deflecting light, the image ray reflecting device having an entrance opening or side for receiving light from a narrow space or an object or objects in a narrow space, a deflecting surface for deflecting light received in the entrance opening or side, and a lower flat surface connecting the entrance opening or side and the deflecting surface, the lower flat surface located in parallel with and contacting, when using the device for visual inspection of narrow spaces or an object or objects in narrow spaces located at a substrate surface, said substrate surface, and an image sensor for detecting light deflected by the image ray reflecting device, wherein the image ray deflecting device has a reflection surface located in an angle in the range of 30°-60° to an optical axis of light incoming to the image ray deflecting device or to an optical axis of light outgoing from the image ray deflecting device.

37. The device of claim 36, wherein the lower flat surface has a width in the range of 0.2-0.6 mm.

38. A device for visual inspection of narrow spaces and objects in narrow spaces at substrate surfaces including:

an image ray deflecting device for deflecting light, the image ray deflecting device having an entrance opening or side and an exit opening or side for light rays, an image sensor for detecting light deflected by the image ray deflecting device, and an illumination system for providing illumination light converging towards the space or the object or objects to be inspected.

39. The device of claim 38, wherein the illumination system is arranged to provide the illumination light in two converging light beams.

40. The device of claim 38, wherein the illumination system is arranged to provide the illumination light in two converging light beams forming an angle of 10-20° to each other.

41. The device of claim 38, wherein the illumination system is arranged to provide the illumination light in two converging light beams forming an angle of 10-20° to each other, as observed in a direction perpendicular to the surface of a substrate when the device is used for visual inspection of a narrow space or an object or objects in a narrow space at the substrate surface.

42. A device for visual inspection of narrow spaces and objects in narrow spaces at substrate surfaces including:

an image ray deflecting device for deflecting light, the image ray deflecting device having an entrance opening or side and an exit opening or side for light rays, an image sensor for detecting light deflected by the image ray deflecting device, and an illumination system for providing illumination light towards the space or object or objects to be inspected, the illumination light issued in directions in the range of 30°-60° in relation to the surface of a substrate when the device is used for visual inspection of a narrow space or an object or objects in a narrow space at the substrate surface.

43. A handheld device for visual inspection of narrow spaces and objects in narrow spaces at substrate surfaces including:

a handheld housing having disposed therein:

an image ray deflecting device for deflecting light having an entrance side and an exit side;

an image sensor for detecting light deflected by the image ray deflecting device;

a plurality of light sources located proximate a transmission path of light from the image ray deflecting device to the image sensor;

a plurality of light guides, each connected to a respective one of the light sources; and wherein said image ray deflecting device further comprises a deflecting surface for deflecting light received at the entrance side and a lower flat surface connecting the entrance side and the deflecting surface, wherein the light guides have lower end portions directing light from their lower end surfaces in directions in the range of 30°-60° in relation to the surface of a substrate when the device is used for visual inspection of a narrow space or an object or objects in a narrow space at the substrate surface.

* * * * *